US011206971B2

(12) United States Patent
Shreim (10) Patent No.: US 11,206,971 B2
(45) Date of Patent: Dec. 28, 2021

(54) OPTICAL SPECTROSCOPY CIRCUITRY FOR ASSESSING EAR HEALTH

(71) Applicant: Cactus Medical, LLC, Irvine, CA (US)

(72) Inventor: Samir Shreim, Irvine, CA (US)

(73) Assignee: Cactus Medical, LLC, Irvine, CA (US)

( * ) Notice: Subject to any disclaimer, the term of this patent is extended or adjusted under 35 U.S.C. 154(b) by 630 days.

(21) Appl. No.: 16/104,095

(22) Filed: Aug. 16, 2018

(65) Prior Publication Data

US 2020/0054203 A1 Feb. 20, 2020

(51) Int. Cl.
| | | |
|---|---|---|
| *A61B 1/227* | (2006.01) | |
| *A61B 5/00* | (2006.01) | |
| *A61B 5/12* | (2006.01) | |
| *A61B 5/01* | (2006.01) | |

(52) U.S. Cl.
CPC ............ *A61B 1/227* (2013.01); *A61B 5/0075* (2013.01); *A61B 5/0084* (2013.01); *A61B 5/01* (2013.01); *A61B 5/12* (2013.01)

(58) Field of Classification Search
CPC ......... A61B 1/227; A61B 1/0684; A61B 1/07; A61B 5/0086
USPC .................................................. 362/572–575
See application file for complete search history.

(56) References Cited

U.S. PATENT DOCUMENTS

| | | | |
|---|---|---|---|
| 5,460,182 A | 10/1995 | Goodman et al. | |
| 5,714,832 A | 2/1998 | Shirrod et al. | |
| 7,058,441 B2 | 6/2006 | Shahar et al. | |
| 9,788,712 B2 | 10/2017 | Seth et al. | |
| 9,918,622 B2 | 3/2018 | Seth et al. | |
| 9,993,142 B2* | 6/2018 | Salman ............... | A61B 1/00137 |
| 2002/0087084 A1 | 7/2002 | Shahar et al. | |
| 2005/0228231 A1 | 10/2005 | MacKinnon et al. | |
| 2006/0282009 A1* | 12/2006 | Oberg .................. | A61B 5/0084 |
| | | | 600/559 |
| 2009/0124873 A1* | 5/2009 | Uchida ................. | A61B 5/0086 |
| | | | 600/310 |
| 2013/0096539 A1* | 4/2013 | Wood ..................... | A61B 90/00 |
| | | | 606/1 |
| 2013/0168532 A1 | 7/2013 | Schmid et al. | |

FOREIGN PATENT DOCUMENTS

| | | |
|---|---|---|
| WO | 2009157825 A1 | 12/2009 |
| WO | 2019226701 A1 | 11/2019 |

OTHER PUBLICATIONS

PCT/US2019/044843 filed Aug. 2, 2019 International Search Report and Written Opinion dated Dec. 4, 2019.

* cited by examiner

*Primary Examiner* — William J Carter
(74) *Attorney, Agent, or Firm* — Rutan & Tucker, LLP (57) ABSTRACT

A diagnostic tool, such as an otoscope or other hand-held diagnostic device features a handle, a head portion and a circuit. The handle includes a controller and the head portion includes one or more optical spectroscopy (OS) components including at least one light detection element. The circuit includes one or more portions configured to be contorted at acute through reflex angles while maintaining electrical connectivity between the controller and the one or more OS components. The circuit includes a first contact area for the at least one light detection element.

20 Claims, 7 Drawing Sheets

OPTICAL SPECTROSCOPY CIRCUITRY FOR ASSESSING EAR HEALTH

FIELD

Embodiment of the disclosure relates to the field of electronics. More particularly, embodiments of the disclosure relate to a flexible circuit for placement within an optical spectroscopy (OS) tool for assessing the health condition of an ear.

GENERAL BACKGROUND

The Otitis Media (OM), or middle ear inflammation is the second most common cause for pediatrician office visits after the common cold. OM accounts for over 20 million office visits per year in the United States alone, with 75% of these being children under 3 years old. Acute Otitis Media (AOM) is a common, usually painful, type of OM that results from an abrupt onset infection for which antibiotics are usually prescribed. Given that AOM inflicts young children, especially children under three years of age, AOM is frequently misdiagnosed.

Poor diagnostic accuracy of AOM results from several factors. Initially, a physical examination is conducted using an otoscope to visually inspect the middle ear of a feverish child having an earache. During evaluation of a patient for AOM, in many cases, a clinician may need to remove cerumen (ear wax) from the patient's ear canal to better inspect the middle ear. However, a busy clinician examining an uncooperative, crying young patient with exasperated parent(s) rarely has the opportunity to remove the cerumen. Where the clinician is provided an opportunity to remove cerumen, such removal is normally conducted abruptly causing further irritation (redness) to the ear canal. Given these examination difficulties, it is often that any sign of redness in the ear leads to a diagnosis of AOM with antibiotics being prescribed.

Despite these challenges, accurate diagnosis of AOM is achievable with current technology, provided the middle ear can be clearly visualized and measurement of ear drum mobility (i.e., assessing presence of middle ear fluid) can be conducted. This can be accomplished by acoustic tympanometry, which requires an airtight seal between a pneumatic otoscope and ear canal for approximately 20 seconds. Acoustic tympanometry involves the modulation of pressure on the ear drum to assess its mobility, which is reduced if fluid is present (indicative of OM). However, this technique is not widely used by primary care physicians, where many OM diagnoses occur because, in practice, pneumatic otoscopy and acoustic tympanometry are virtually impossible to accomplish on a resistant patient. Also, such techniques may be quite painful for a young patient due to requisite cleaning of the ear canal to remove cerumen is needed for accurate determination of OM.

Several clinical and home devices are also available to improve OM diagnosis. These include a hand-held device that assesses ear drum mobility using sound (EarCheck), and several magnifying smartphone attachments (e.g. CellScope). Importantly, while development and sale of smartphone attachments indicates market interest, they have not achieved widespread consumer or clinical adoption because they do not address how to accurately and easily diagnose a normally resistant young child, especially when the results are compromised when ear wax is not removed from the patient. Consequently, EarCheck and CellScope are prone to inaccurate diagnoses, erosion of user trust, limited adoption, and unreliable results.

Lastly, while visual inspection for OM may assist in determining the presence of OM, recent technology has been developed to utilize reflected light in accordance with optical spectroscopy (OS) technologies to assess the health of the middle ear, as described in U.S. Patent Application No. 62/675,056 entitled "Light-Emitting Diode Based Diffuse Optical Spectroscopy Tool For Assessing the Ear," filed on 22 May 2018. The usage of reflected light technology greatly improves accurate diagnosis of OM without removal of ear wax and is performed quickly, without approximately 20 seconds of an airtight seal between the pneumatic otoscope and ear canal as described above. However, to perform reflected light analysis using OS technologies, especially within a hand-held device, a circuitry architecture is needed that allows for placement and retention of the OS technologies within a limited spacing of the hand-held device (e.g., otoscope) and, in some deployments, allows for easily adjustment of the circuitry to avoid disturbance of the integrated optical logic that provides visualization.

BRIEF DESCRIPTION OF THE DRAWINGS

Embodiments of the invention are illustrated by way of example and not by way of limitation in the figures of the accompanying drawings, in which like references indicate similar elements and in which.

DETAILED DESCRIPTION

One embodiment of the disclosure is directed to a circuit for deployment within a hand-held, non-invasive diagnostic tool, such as an otoscope for example. In accordance with a first embodiment of the disclosure, the circuit may be formed with a "flexible" structure (e.g., the circuit capable of being contorted in one or more acute-through-reflex angles such as more than thirty degrees, and in some cases in obtuse angles, without damaging the circuit). However, in accordance with a second embodiment of the disclosure, one or more portions of the circuit may be formed with a flexible architecture while the remaining portion(s) of the circuit may be formed with a "rigid" structure (e.g., the circuit incapable of being contorted more than five degrees without being damaged). The selected level of flexibility is sufficient to allow the circuit to be contorted into a selected geometry for placement within a head portion of the diagnostic tool.

The selected geometry orients certain electronic components used for optical spectroscopy (OS) analysis (hereinafter, "OS components") toward a common point of convergence. Also, the selected geometry enables certain OS components coupled to the circuit, such as an amplifier and at least one light detection element, to be in closer proximity to each other (e.g., less than one centimeter) when the circuit is altered from an unfolded state to a folded state. This placement of the amplifier in closer proximity to at least one light detection element, such as one or more photodiodes for example, reduces signal interference experienced by the photodiode(s). Herein, this circuit is referred to as a "flexible circuit."

As described below, the flexible circuit provides contact areas for mounting OS components that are used to illuminate matter accessible via an ear canal (e.g., portions of the ear canal, tympanic membrane, middle ear cavity, cerumen, air and/or fluid in the middle ear cavity, etc.) as well as detect and collect light returning to the diagnostic tool after interaction (e.g., scatter and/or absorption) with the accessible matter. This captured light, sometimes referred to as the "reflectance spectra," is converted into data, which is provided to hardware circuitry enclosed within a housing of the diagnostic tool (e.g., handle housing of the otoscope). The hardware circuitry features a controller, which analyzes the data to assess characteristics (e.g., a parameter or combination of parameters such as shape, magnitude, etc.) of the reflectance spectra associated with the captured light for use in detecting a health condition of the middle ear. More specifically, according to one embodiment of the disclosure, the assessed characteristics may be compared to data associated with reflectance spectra for healthy ears and/or data associated with reflectance spectra for ears with health conditions including different types of Otitis Media (OM), such as Acute Otitis Media (AOM) or Otitis Media with effusion (OME) for example.

Stated differently, the OS components mounted on the flexible circuit, in combination with the above-described hardware circuitry, utilizes returned (e g, reflected) light to detect tissue properties. Light incident on turbid media, such as the eardrum or infected middle ear for example, is both absorbed and scattered. This creates a diffuse and unique reflective (and chromatic) spectra, which may be subsequently used as a spectral reference profile. Matter residing in the middle ear absorbs and scatters light in a particular way that may be assessed spectrally. Importantly, the diffuse nature of OS enables measurements in situations that preclude imaging, such as an ear canal occluded by wax. Provided the path length is long enough that transmitted or back-reflected light is diffuse, the Beer-Lambert Law provides the diagnostic tool with an accurate approximation to quantitatively determine the concentration of tissue chromophores:

$$I(\lambda) = I_0(\lambda) 10^{-\mu'_s(\lambda) l - (\sum_i \mu_{a,i}(\lambda)) l} \qquad \text{Equation (1)}$$

where "$I(\lambda)$" is the measured light intensity as a function of wavelength $\lambda$, "$I_0(\lambda)$" is the incident intensity, "$\mu_{a,i}(\lambda)$" is the $i^{th}$ chromophore's absorption coefficient, "$\mu'_s(\lambda)$" is the scattering coefficient and "l" is the optical path length. Herein, the provided "$\mu_{a,i}(\lambda)$" is known (e.g., oxy- and deoxyhemoglobin) and scattering and path length can be estimated, inversion of Equation (1) provides accurate, quantitative information on tissue properties.

It is contemplated that traditional OS technologies requiring sophisticated optics and signal processing to perform the above-described analysis are expensive and bulky. In contrast, the deployment of the flexible circuit enables the OS components to be implemented into a head portion of a diagnostic tool. The diagnostic tool may be broadly defined as any hand-held measurement device that analyzes the health of an individual (e.g., tissue within a body cavity such as the middle ear, throat, intestine, etc.) through analysis of assess characteristics gathered from the reflected light for comparison with data associated with prior measured reflectance spectra for healthy tissue and/or data associated with prior measured reflectance spectra for tissue with health conditions such as tissue within the middle ear with some form of Otitis Media for example.

The diagnostic tool may be deployed as an otoscope, endoscope, microscope or another type optical-based clinical device that includes OS components oriented in accordance with the selected geometry, as described above. As an optional feature, the diagnostic tool may include video capturing logic to capture an optical image or a series of optical images (e.g., video) and/or video rendering logic to display the image or the series of images (collectively referred to as "video logic"). Additionally, or in the alternative, the diagnostic tool may include a network interface that enables a transfer of image(s) from the diagnostic tool to a remote computing device via a network. The network interface may provide wireless connectivity to the network or may provide a physical connector for coupling to a cellular telephone for use in transferring the image(s) to the remote computing device (e.g., server, cellular phone, computer, wearable, etc.) of a health service provider, insurance company, pharmacy department, or the like.

According to one embodiment of the disclosure, the diagnostic tool may be implemented as an otoscope, which provides visual analysis of the features of the ear along with automated OS inspection of the ear. The automated OS inspection may be performed by non-imaging optics in to improve diagnostic accuracy as well as augment otoscope functionality. All data may be collected through the use of OS components including one or more spectral illumination light sources and light detection elements, which may be positioned on the flexible circuit and, after angular contortion of the flexible circuit at acute through obtuse angles, housed in an otoscope form-factor used for clinical examinations of the middle ear. The spectral illumination light source(s) (e.g., one or more light emitting diodes "LEDs") are for emitting incident light into the middle ear cavity, while the one or more light detection elements are used to collect returning light, which may be measured using OS components. For example, the spectral illumination light source(s), referred to as a "spectral light source," may include, but is not limited or restricted to one or more LEDs, laser diodes, vertical cavity surface emitting lasers (VCSELs), and/or broadband (e.g., incandescent, fluorescent, etc.) light sources. The one or more light detection elements may include, but is not limited or restricted to photodiodes (e.g., silicon and InGaAs), spectrometers on a chip (e.g. CCD and CMOS based spectrometers on a chip), or the like.

In the following description, numerous specific details are set forth. However, it is understood that embodiments of the disclosure may be practiced without these specific details. For instance, besides the middle ear as described herein, the diagnostic tool deploying the flexible circuit may be configured for use with assessing the health condition of other body part including, but not limited to a throat, skin, body cavities accessed and/or imaged by endoscopy, or those exposed during surgery. In other instances, well-known structures and techniques have not been shown in detail in order not to obscure the understanding of this description. Those of ordinary skill in the art, with the included descriptions, will be able to implement appropriate functionality without undue experimentation.

References in the specification to "one embodiment" or "an embodiment," may indicate that the embodiment described may include a particular feature, structure, or element, but every embodiment may not necessarily include that particular feature, structure, or element. Moreover, such phrases are not necessarily referring to the same embodiment. Further, when a particular feature, structure, or element is described in connection with an embodiment, it is submitted that such feature, structure, or element may be deployed in connection with other embodiments whether or not explicitly described.

Lastly, the terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Any feature or combination of features described herein are included within the scope of the invention provided that the features included in any such combination are not mutually inconsistent as will be apparent from the context, this specification, and the knowledge of one of ordinary skill in the art. Additional advantages and aspects of the present invention are apparent in the following detailed description and claims. Stated differently, this invention is susceptible to embodiments of many different forms, and thus, it is intended that the disclosure be considered as an example of the principles of the invention and not intended to limit the invention to the specific embodiments shown and described.

I. General Architecture—Diagnostic Tool

Figure 1:
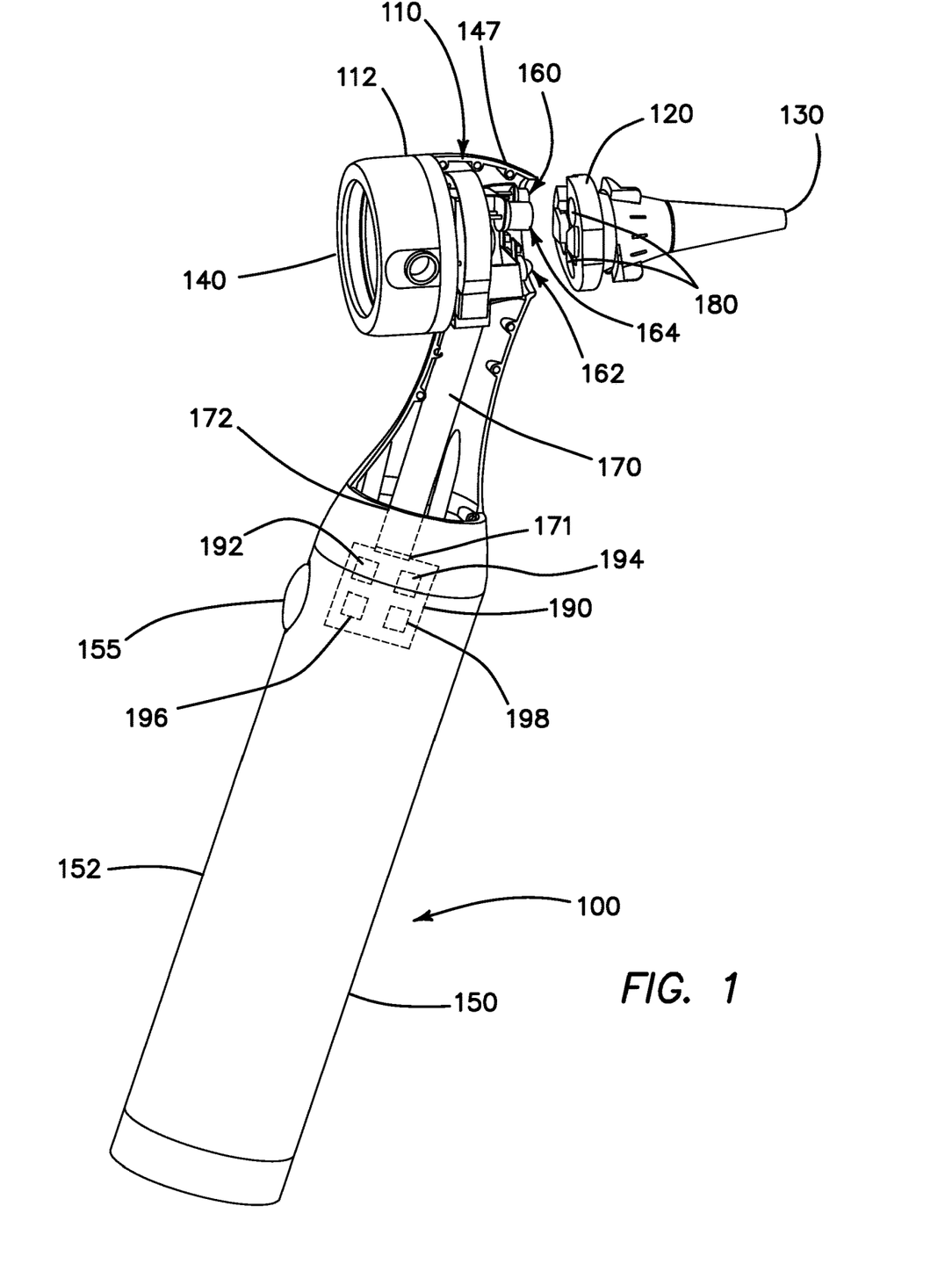
FIG. 1 is a first illustrative embodiment of a diagnostic tool featuring a flexible circuit to retention of electronic components for optical spectroscopy.

Referring to FIG. 1, a first illustrative embodiment of a non-invasive, diagnostic tool 100 for diagnosing health conditions, such as ear conditions irrespective of presence of cerumen in an ear canal, is shown. The diagnostic tool 100 may be adapted as an otoscope integrated with a head portion 110, an interface 120, a speculum 130, visualization optics 140, a handle 150, and a measure button 155. An example of the diagnostic tool 100 may be an otoscope modified with circuitry for receiving light returning from the ear canal and measuring reflectance intensity.

Coupled to the interface 120, the removable speculum 130 may be inserted into an ear canal of a patient. For this embodiment of the diagnostic tool 100, the speculum 130 allows for visualization a portion of a body cavity (e.g., an ear cavity) using the visualization optics 140. Additionally, the diagnostic tool 100 also provides a pathway to emit incident light from and collect returning light by the OS components 160.

The OS components 160 are arranged into position by and secured to a flexible circuit 170 within the head portion 110 for placement within spacings 180 (pockets) preformed in the interface 120 for alignment with the light pathway provided by the speculum 130. The electronic components 160 may include an illumination assembly 162 (e.g., one or more spectral light sources) positioned to illuminate the ear canal with incident light at predetermined wavelengths. The predetermined wavelengths are selected to diagnose specific ear conditions.

Additionally, the OS components 160 may include a detection assembly 164, which may be configured as one or more light detection elements (hereinafter, "light detection element(s)") configured to receive light returning from the ear canal and measure a reflectance intensity as a function of the predetermined wavelengths to diagnose a presence of OM. For this embodiment, the light detection element(s) 164 may include one or more photodiodes with distinct spectral sensitivities, where the spectral light source 162 may feature one or more LEDs having spectral distributions that overlap each photodiode sensitivity and may be illuminated concurrently (i.e. at least partially overlapping in time). Concurrent illumination may achieve reduced measurement time without crosstalk.

The measure button 155 is situated to protrude from an outer surface 152 of the handle 150. The measure button 155 activates the spectral light source 162 and/or light detection element(s) 164 as described below. The measure button 155 may be included in any other location positioned on the diagnostic tool 100.

More specifically, according to one embodiment of the disclosure, the flexible circuit 170 is adapted for connection to control circuitry 190 including a power source 192, controller 194 and a network interface 196. The flexible circuit 170 includes a first end 172 and a second end 174 positioned at an opposite end of the flexible circuit 170 (see FIG. 2). The first end 172 is coupled to connector 171, which provides an electrical coupling with the control circuitry 190. The second end 174 is coupled to an amplifier (not shown). Upon contorting the flexible circuit 170 for placement within a housing 112 of the head portion 110, the amplifier is positioned in close proximity to light detection element(s) 164 (e.g., photodiodes) mounted on one or more of circuit segments of the flexible circuit 170 to minimize (or at least reduce) noise causing signal interference from the surrounding environment.

Although not shown in detail herein, but illustrated in greater detail in FIG. 2, the flexible circuit 170 includes protruding segment with contacts for mounting accessories (e.g., electronic components) that subsequently reside within the head portion 110. These accessories are installed to receive reflected light from a body cavity (e.g., ear canal), transmit light for OS detection based on the reflected light or visual inspection, and/or measure temperature. For instance, for an embodiment of the flexible circuit 170 described below, the light detection element(s) 164 may be coupled to neighboring circuit segments, the spectral light source(s) may be coupled to a circuit segment, and white light sources may be coupled to a pair of sub-segments extending from the circuit segment including the spectral light source. In some embodiments, the spectral light source 162 may comprise one or more of light-emitting diodes (LEDs), laser diodes, or vertical-cavity surface-emitting laser (VCSELs), and wherein each LED element, laser diode, laser diode or VCSEL comprises a central wavelength matching with a specific wavelength of the predetermined wavelengths.

It is contemplated that the organization of circuit segment and/or accessories may vary depending on the resultant circuit configuration needed after folding and placement of the flexible circuit within the otoscope head housing. Stated differently, the shape of the flexible circuit 170 is specifically intended to fold in a manner suitable for assembling accessories (e.g., OS components 160 supporting OM reflected light detection) into the head portion 110. The flexible circuit 170 is shielded to further minimize noise.

In some embodiments, the predetermined wavelengths may be selected from a range of wavelengths between about 400 nanometers (nm) and 2000 nm. In some embodiments, the one or more light detection elements may comprise photodiodes, photomultiplier tubes (PMT), complementary metal-oxide-semiconductor (CMOS) arrays, charge-coupled device (CCD) arrays, spectrometers, and fabry-perot interferometers. For this disclosure, the light detection element(s) will be described as photodiodes, although it is contemplated that other types of light detection elements, as described above, may be used additionally or as an alternative.

According to one embodiment of the disclosure, at least two photodiodes with complementary spectral sensitivities are utilized to span the required spectral range. In some of these embodiments, the complementary sensitivities may partially overlap. For example, a first photodiode, being part of the light detection element(s) 164, may be deployed as a silicon photodiode that is sensitive to a spectral (wavelength) ranging from approximately 400 nm-1100 nm. A second photodiode, being part of the light detection element(s) 164, may be deployed as an InGaAs photodiode that is sensitive to a spectral range of approximately 900 nm-1700 nm.

According to another embodiment of the disclosure, a single photodiode may be implemented as the light detection element(s) 164. For this embodiment, a silicon photodiode with a spectral sensitivity between 400-1100 nm may be utilized in lieu of a plurality of photodiodes. As an optional feature, the single photodiode may be "enhanced" to either (1) extend the sensitive range or (2) increase the output signal of the photodiode within the sensitive range. More specifically, the photodiode may be enhanced in the infrared wavelength, which enables light sensitivity to detect light exceeding 1100 nm wavelength. Additionally, or in the alternative, the photodiode may be enhanced in the visible/UV wavelengths, which improve sensitivity of detected light at wavelengths less than 400 nm.

In some embodiments, the reflected light analysis conducted by the controller 194 may comprise comparing characteristics of the reflectance spectra determined from the reflected light collected by the light detection element(s) 174 to data associated with known reflectance spectra associated with healthy and/or unhealthy ear conditions (i.e., one or more reference metric distributions). Each reference metric distribution may be determined based on machine learning or heuristics that considers data from one or more prior analysis of ear conditions. The reference metric distributions may be stored locally in the memory of the processing unit or downloadable from a remote database.

Figure 7:
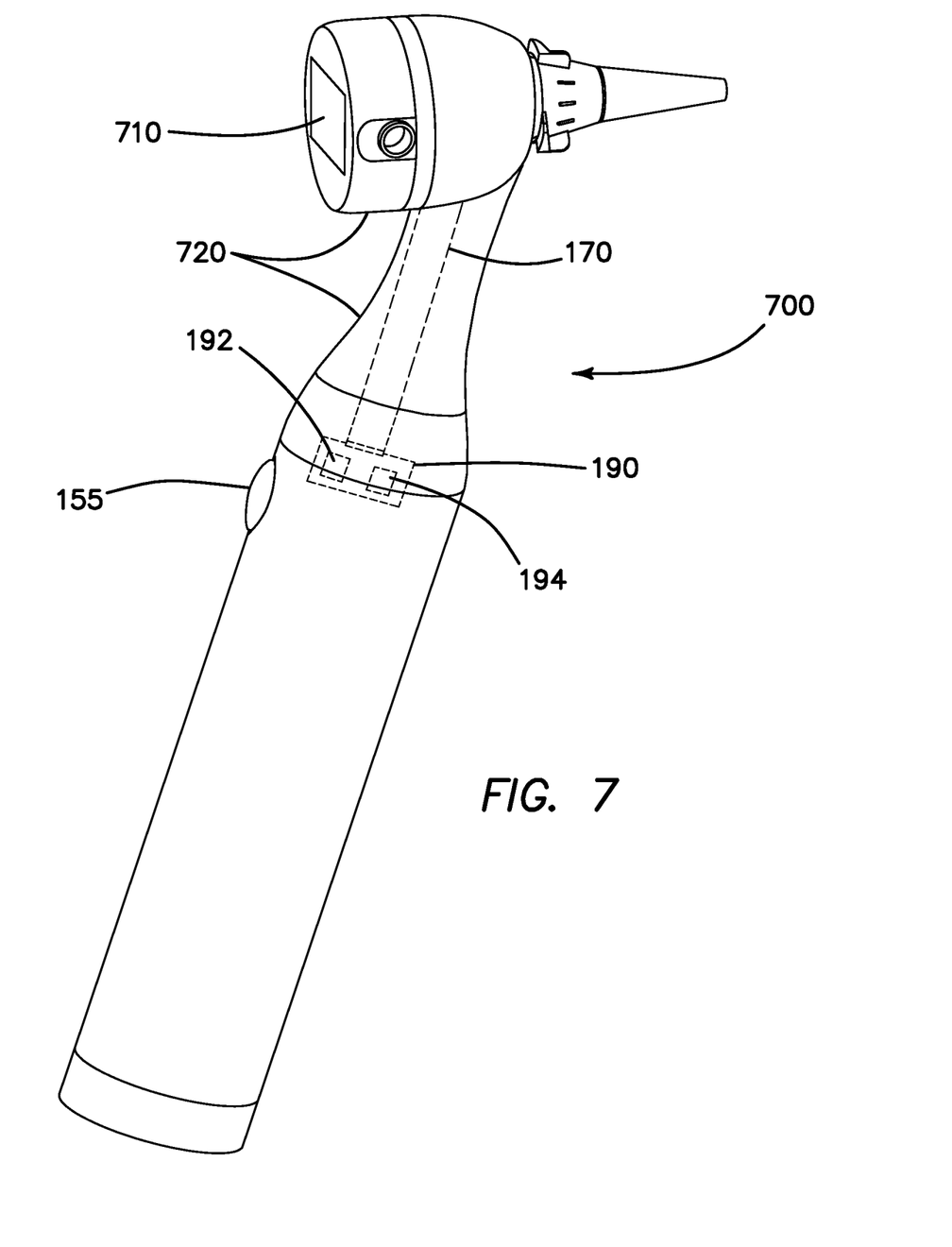
FIG. 7 is a second illustrative embodiment of a diagnostic tool featuring the flexible circuit to retention of electronic components specific to optical spectroscopy without the visualization optics.

While the diagnostic tool 100 is directed to detection of acute otitis media (AOM), as described above, this tool 100 may additionally include visualization optics 140, including one or more brightfield light sources configured to illuminate the ear canal for visual evaluation and a plurality of optical diffusers in line with the brightfield light sources configured to diffuse light from the brightfield light sources into the ear canal. Also, in addition or alternatively to the visualization optics 140, the diagnostic tool 100 may include video logic (not shown), which may include (i) video capturing logic to capture an optical image or a series of optical images (e.g., video) for storage within a storage memory 198 and/or (ii) video rendering logic to display the image or the series of images on a screen 710 as shown in FIG. 7.

In summary, the flexible circuit 170 is configured for partial placement with a head portion 110 of the diagnostic tool (e.g., otoscope head 110 or hand-held measurement unit) to properly position the OS components 160 to (i) emit incident light, (ii) collect returning light (e.g., scattered, reflected light), and/or (iii) analyze signals arising from various ear conditions. Different matter within the ear may constitute a set of optical contrasts, each contributing to the magnitude of the reflectance spectra. For example, hemoglobin species contribute to erythema (redness), lipid species constitute wax and create spectral differences pronounced but not limited to blue/green, water content of middle ear effusions create contrast in the infrared, etc. Hence, some or all of these ear characteristics may contribute to changes in reflectance due to their optical properties (e.g. scattering and absorption). These optical properties may vary in a consistent way with different types of ear pathology. In essence, waxy healthy, waxy infected, clean healthy, and clean infected ears each constitute populations with statistically separable reflectance spectra. Herein such information is collected at only the wavelengths needed to make the distinction, avoiding redundant measurements. This leads to a more statistically robust measurement.

II. General Architecture—Flexible Circuit

Figure 2:
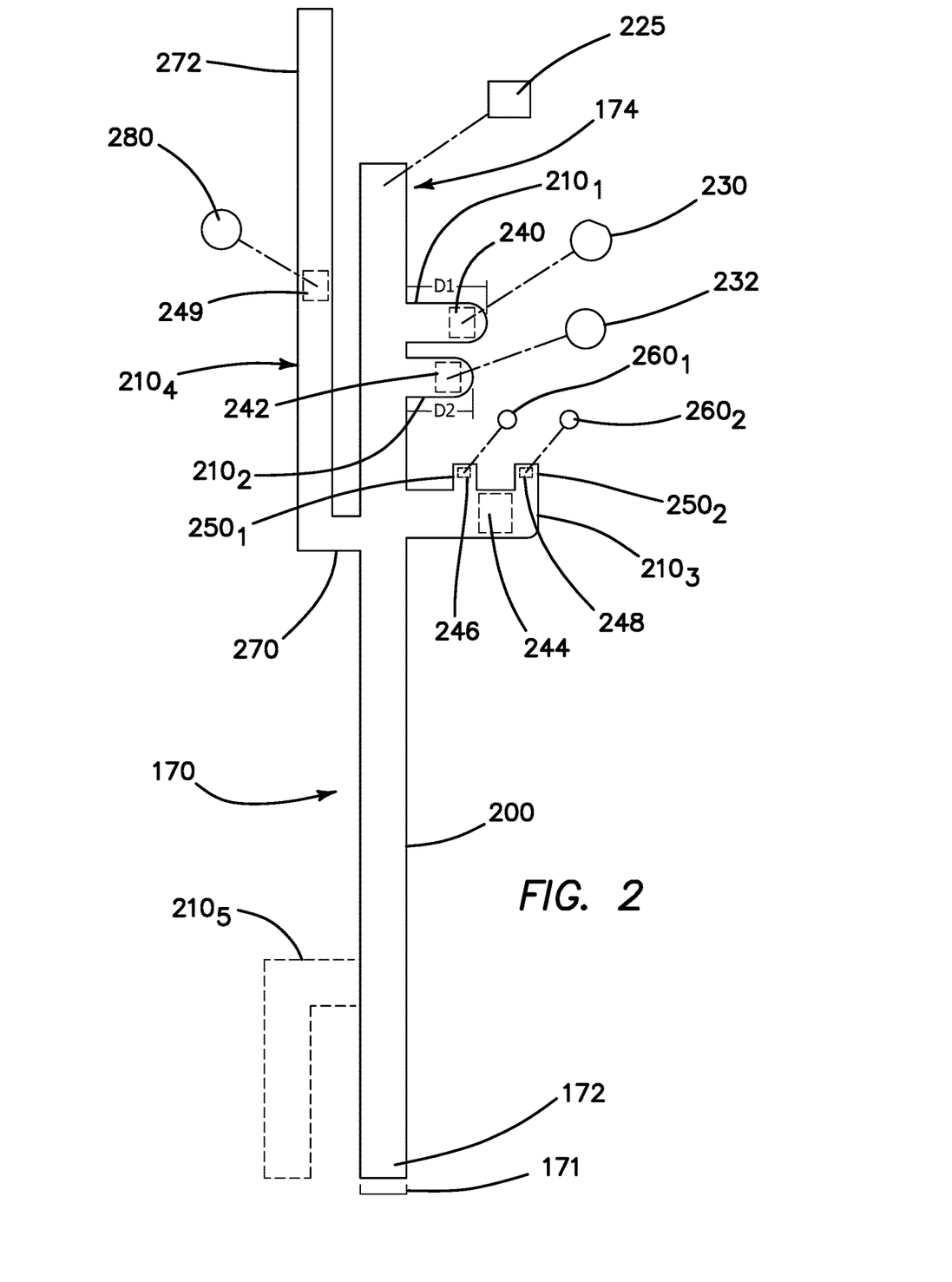
FIG. 2 is a plan view of a first exemplary embodiment of the flexible circuit in an unfolded state.

Referring to FIG. 2, an illustrative embodiment of the flexible circuit 170 featuring components to perform optical spectroscopy (OS) on matter within an ear canal to detect different type of health conditions of the ear (e.g., Otitis Media "OM") is shown. According to this embodiment of the disclosure, the flexible circuit 170 includes a main circuit segment 200 (referred to as the "main segment") and a plurality of circuit segments $210_1\text{-}210_N$ (N≥1) extending therefrom. The main segment 200 is adapted for connection to the control circuitry 190 (e.g., power source 192, controller 194 network interface 196, and/or storage memory 198) positioned within the handle 150 of the diagnostic tool 100 (see FIG. 1), such as an otoscope or similarly constructed, hand-held diagnostic tool. Each of the circuit segments $210_1\text{-}210_N$ may be adapted with one or more contact areas to receive OS components 160 that are positioned within the housing of the head portion 110 of the diagnostic tool (e.g., otoscope head 110 of FIG. 1).

Figure 5:
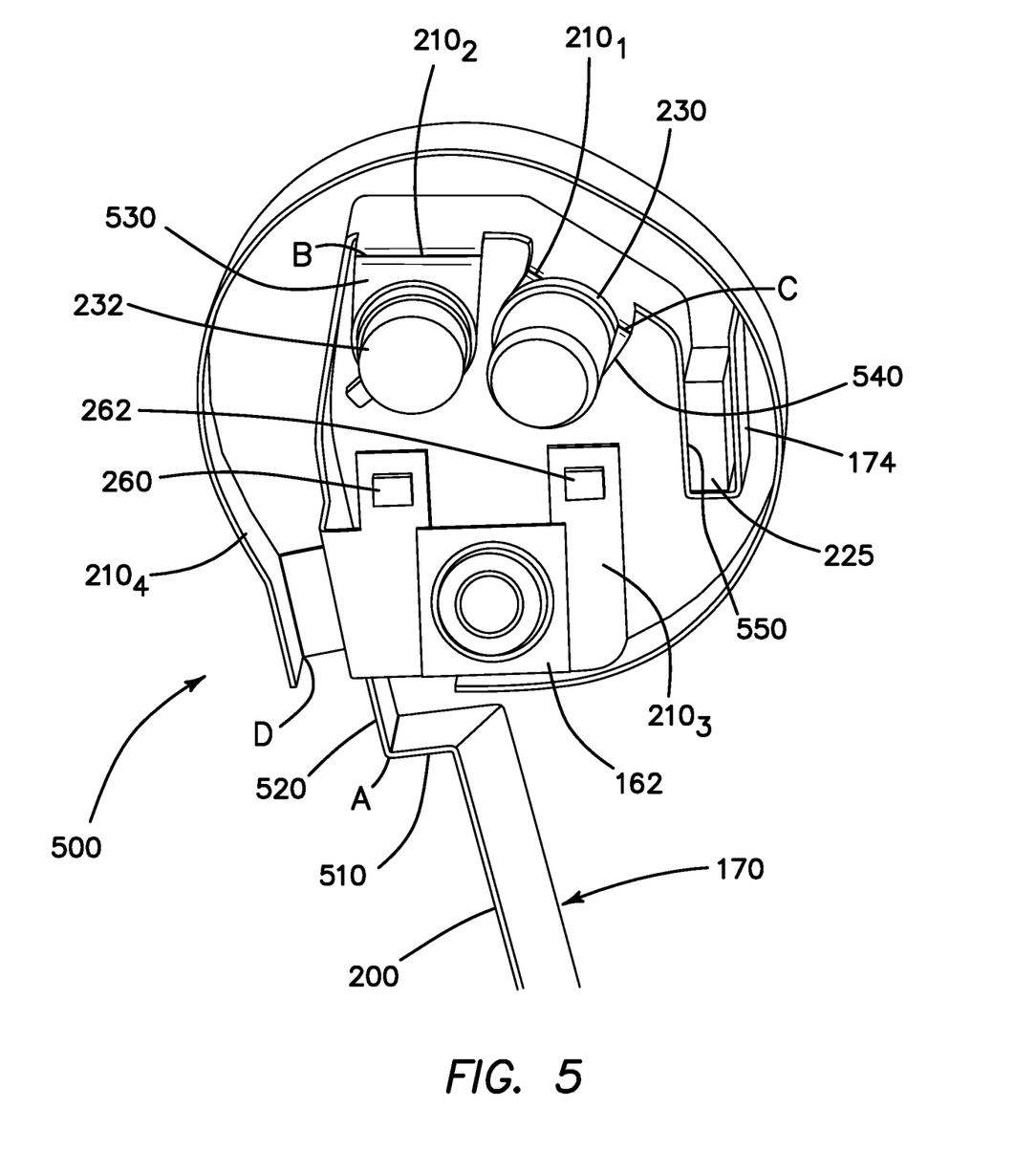
FIG. 5 is a perspective view of a pattern of the flexible circuit configured in the folded state and installed within a head portion of a diagnostic tool of FIG. 1 or FIG. 7.
Figure 6:
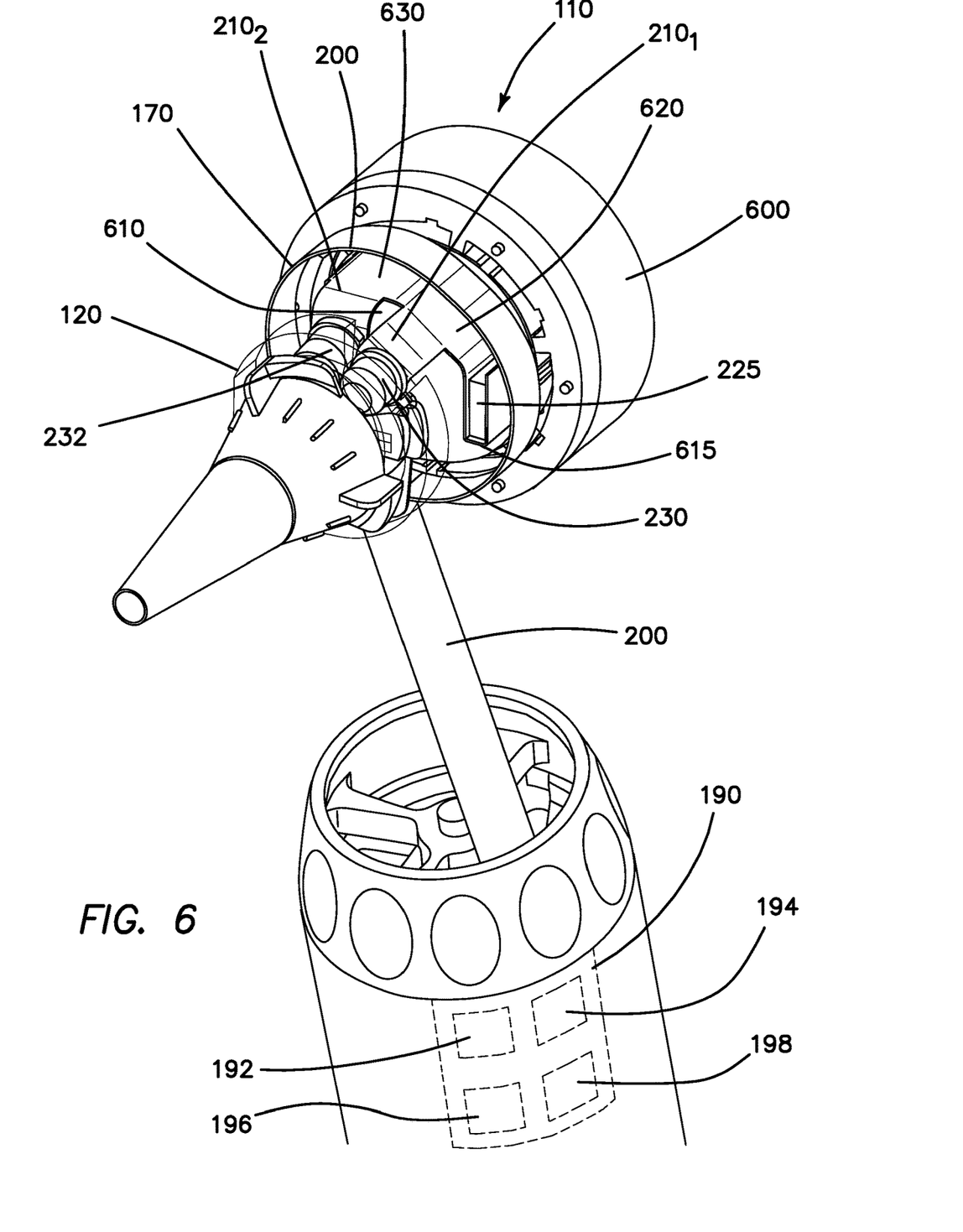
FIG. 6 is a perspective view of the flexible circuit of FIG. 5 installed within a head portion of the diagnostic tool of FIG. 1 or FIG. 7.

As shown, the main segment 200 may include (i) the first end 172 for coupling to the control circuitry 190 via the connector 171 and (ii) the second end 174 adapted to receive an amplifier 225. The first end 172 of the main segment 200 is position on an opposite side of the main segment 200 than the second end 174. After placing the flexible circuit 170 into a folded state and installing an upper portion of the flexible circuit 170 into the head portion 110 of the diagnostic tool 100 as shown in FIG. 1, a distance between the amplifier 225 located at the second end 174 of the main segment 200 and the light detection element(s) 164 (e.g., photodiodes 230 and 232) mounted on the circuit segments $210_1\text{-}210_2$ is reduced in order to amplify signaling measured by the photodiodes 230 and 232 and reduce signal interference that may adversely affect OS measurements. Stated differently, after folding of the flexible circuit 170, a distance between the amplifier 225 and the light detection element(s) 164 is less than a distance between the amplifier 225 and the light detection element(s) 164 when the flexible circuit 170 is in an unfolded state as illustrated in FIG. 2. As shown in FIGS. 5-6, in a folded state, the amplifier 225 is positioned laterally from the photodiodes 230 and 232.

Referring still to FIG. 2, each of the plurality of circuit segments $210_1\text{-}210_N$ includes contact areas for mounting one or more electronic components that subsequently reside within the head portion of the diagnostic tool (e.g., head portion 110 of FIG. 1). As shown, a first circuit segment $210_1$ extends a first prescribed distance "D1" from the main segment 200 while a second circuit segment $210_2$ extends a second prescribed distance "D2" from the main segment 200, where "D1" is greater than "D2". As the first circuit segment $210_1$ is positioned closer to the second end 174 of the main segment 200 than the second circuit segment $210_2$, one or more electronic components mounted on the first circuit segment $210_1$ may be positioned closer in distance to the amplifier 225 after contorting the first circuit segment $210_1$ and a portion of the main segment 200 toward the second end 174 during installation within the head portion of the diagnostic tool. More specifically, as shown, the first circuit segment $210_1$ is configured with a first contact area 240 to receive the first photodiode 230 mounted thereon. The second circuit segment $210_2$ is configured with a second contact area 242 to receive a second photodiode 232 mounted thereon.

Positioned between the first end 172 of the main segment 200 and the second circuit segment $210_2$, a third circuit segment $210_3$ extends laterally from the main segment 200 at a distance greater than the first circuit segment $210_1$. The third circuit segment $210_3$ is configured with a third contact area 244 to receive the spectral light source 162. Optionally, the third circuit segment $210_3$ may include one or more sub-segments 250 (e.g., sub-segments $250_1$-$250_M$, M≥1) extending from the third circuit segment $210_3$ in a longitudinal direction generally perpendicular to the third circuit segment $210_3$. Herein, as shown, a first sub-segment $250_1$ may include a fourth contact area 246 and a second sub-segment $250_2$ may include a fifth contact area 248, each contact area 246 and 248 is configured to provide electrical connectivity to a corresponding white light source 260 or 262 mounted thereon.

As still shown in FIG. 2, a fourth circuit segment $210_4$ includes a first portion 270 laterally extending from the main segment 200 and a second portion 272 oriented perpendicular to the first portion 270 and substantially in parallel with the main segment 200. The second portion 272 of the fourth circuit segment $210_4$ includes one or more contact areas (e.g., contact area 249) to receive one or more additional electronic components that provide additional functionality other than the OS functionality.

For example, the contact area 249 may be adapted to receive a temperature sensor 280 that measures a temperature of a patient upon which the OS analysis is performed. Additionally, or in the alternative, a pneumatic sensor may be mounted on contact area 249 or another contact area positioned on the second portion 272 of the fourth circuit segment $210_4$. The temperature and pneumatic sensors may collect signals that provide additional data to the controller 194 that performs the diagnostic analysis, where such data may influence a diagnosis result (e.g., temperature greater than a prescribed threshold and a limited correlation between the assessed characteristics and the data associated with measured reflectance spectra may issue a diagnosis of OM in contrast with the temperature less than the prescribed threshold with the same correlation). The results may also be displayed to the user through a display as illustrated in FIG. 7. Segment $210_4$ may also connect to light sources or displays meant to convey information to the user.

As described above, according to one embodiment of the disclosure, in lieu of a single end 170 of the main segment 200 for connectivity to the hardware circuitry 190, it is contemplated that a circuit segment 2105 may be provided to operate as a second connector. This facilitates a modular design that simplifies product architecture and reduces the cost of manufacture.

As another embodiment of the disclosure, in lieu of the entire flexible circuit 170 being capable of being contorted (e.g., bent and/or twisted) in different angles, it is contemplated that the flexible circuit 170 may have a hybrid architecture. For example, a first portion of the flexible circuit 170 (e.g., circuit segments $210_1$-$210_N$ and a portion of the main segment 200 between the second end 174 and a point of intersection with the fourth circuit segment $210_4$) may be flexible (e.g., capable of being contorted more than thirty degrees, and in some cases more than ninety degrees, without damaging the circuit). However, a remainder of the flexible circuit 170 (e.g., main segment 200 between the point of intersection and the first end 172) may be formed of a rigid (non-bendable) material.

Figure 3:
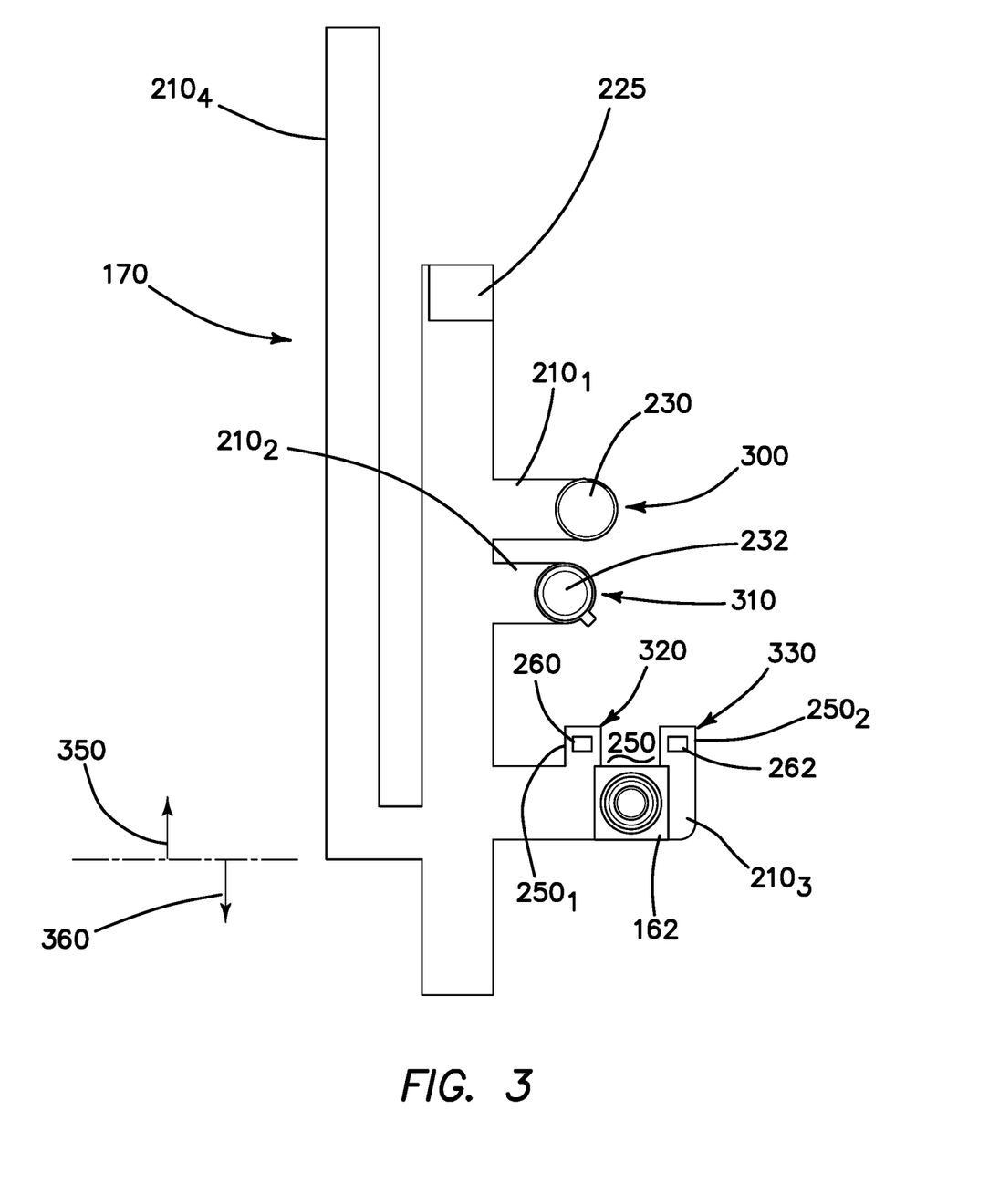
FIG. 3 is a plan view of the flexible circuit of FIG. 2 including components that produce reflectance spectra.

Referring now to FIG. 3, a plan view of the flexible circuit 170 of FIG. 2 assembled to include the electronic components 170 to perform optical spectroscopy (OS) by generating incident light of prescribed wavelength, collecting reflected light, and generating data for comparison with measured reflectance spectra is shown. Herein, the first photodiode 230 is positioned that a distal end 300 of the first circuit segment $210_1$, and the second photodiode 232 is positioned that a distal end 310 of the second circuit segment $210_2$. Also, a first white light source 260 is positioned at a distal end 320 of the first sub-segment $250_1$, which is one of the sub-segments 250 configured as part of the third circuit segment $210_3$. A second white light source 262 is positioned at a distal end 330 of the second sub-segment $250_2$ to provide light for visualization of the ear cavity. The spectral light source 162 is positioned on the third circuit segment $210_3$ interposed between the first sub-segment $250_1$ and the second sub-segment $250_2$.

As further shown, the amplifier 225 is positioned at the second end 174 of the main segment 200. The first photodiode 230, the second photodiode 232 and the amplifier 225 are positioned on an upper half portion 350 of the flexible circuit 170. Based on this positioning, upon folding circuit segments $210_1$-$210_4$ of the upper half portion 350 of the flexible circuit 170, the amplifier 225 is placed in closer proximity to the first photodiode 230 and the second photodiode 232 than in an unfolded state. Therefore, the folding of the flexible circuit 170 may take advantage of the insulative/shielding properties provided by material within the upper and lower layers of the circuit 170 to isolate the amplifier 225.

As illustrated, FIG. 3 shows the attachment of the photodiodes 230 and 232, the spectral light source 162 and white light sources 260 and 262 to different segments $210_1$-$210_3$ or sub-segments $250_1$-$250_2$ of the flexible circuit 170. However, as another embodiment, it is contemplated that one or more of these OS components may be initially assembled within the head portion 110 and/or the interface 120 of the diagnostic tool 100 and attached to the flexible circuit 170 subsequently. For example, the photodiodes 230 and 232 may be placed within cylindrical spacing 180 that are formed within the interface 120 of the hand-held diagnostic tool 100 of FIG. 1, where the photodiodes 230 and 232 may be coupled (e.g., soldered, etc.) to the flexible circuit 170 during installation of the flexible circuit 170 into the head portion 110 of the hand-held diagnostic tool 100.

Figure 4:
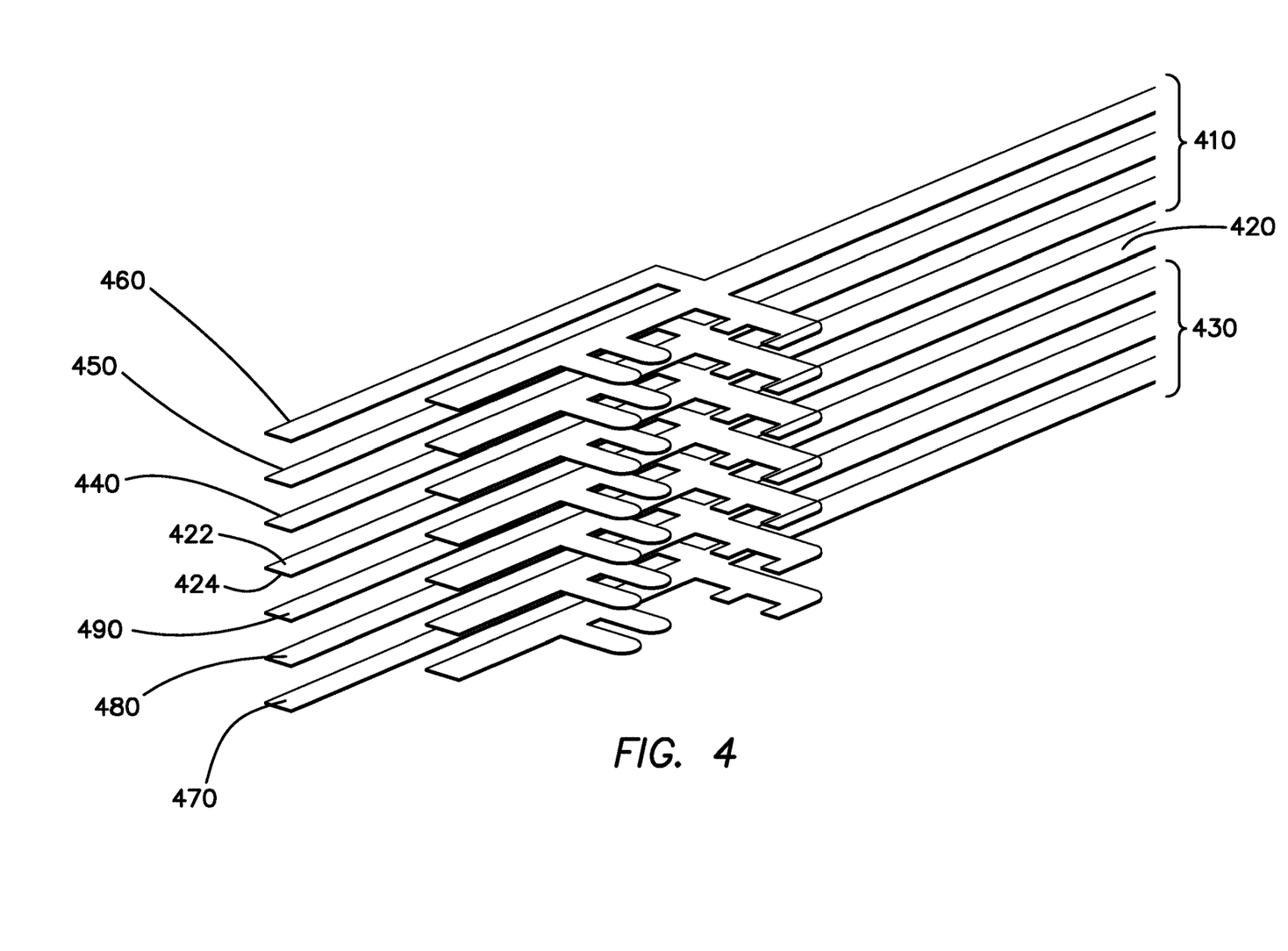
FIG. 4 is a perspective view of layers forming the flexible circuit of FIG. 2.

Referring to FIG. 4, a perspective view of circuit layers forming an embodiment of the flexible circuit 170 of FIG. 1 is shown. Herein, the flexible circuit 170 includes a plurality of layers 400 with a top layering scheme 410 of the flexible circuit 170 positioned over a trace layer 420. The trace layer 420 provides a communication medium for signaling and/or a medium for directing current to illuminate the photodiodes 230 and/or 232 of FIG. 3. A bottom layering scheme 430 operates as a mirrored representation of the top layering scheme 410 of the flexible circuit 170.

According to one embodiment of the disclosure, the top layering scheme 410 includes a first insulation layer 440 coupled by adhesive to a top surface 422 of the trace layer 420. Attached to and positioned over the first insulation layer 440, a shielding layer 450 is provided. The shielding layer 450 may be made of a copper or other conductive material, which is positioned between the first insulation layer 440 and a second insulation layer 460 to reduce signal distortion caused by environmental conditions (e.g., nearly alternating current "AC" lines, etc.). Similarly, positioned below the trace 420, the bottom layering scheme 430 includes a third insulation layer 470, conductive shielding layer 480 and fourth insulation layer 490 positioned below and coupled to a bottom surface 424 of the trace layer 420.

Although not shown, as another illustrative embodiment, it is contemplated that (i) shielding 450 and the second insulation layer 460 and/or (ii) the shielding layer 480 and the third insulation layer 490 may be combined to form a combination insulation/shielding layer. This alternative embodiment reduces the number of layers forming the flexible circuit 170 to five layers in lieu of seven layers as shown in FIG. 4. Moreover, portions of the flexible circuit 170, based on the folded geometry used for placement within the head portion 110 of the hand-held diagnostic tool (e.g., otoscope head 110 of FIG. 1), may provide further shielding between the amplifier 225 and noise sources (e.g. AC lines).

In lieu of the architecture as shown in FIG. 4, it is contemplated that the flexible circuit 170 may be substituted for waveguides (e.g., plastic or glass optical fibers), which may feature different levels of flexibility. For example, the waveguides may be constructed with a first level of flexibility (e.g., highly flexible to support directional changes in acute-through-reflex angles, including obtuse angles), a second level of flexibility (e.g., rigid to support no directional change exceed five (5) degrees), or any combination thereof. A first end of each waveguide may be coupled to a corresponding OS component while a second end of the waveguide may be configured to emit and/or receive light for optical spectroscopy.

Referring now to FIG. 5, a perspective view of a folded pattern 500 of the flexible circuit 170 to be installed within a head portion of a hand-held diagnostic tool is shown. Herein, the folded pattern 500 features a first portion 510 of the main segment 200 that, predominantly at transverse A, is angularly contorted along an axis running along the width of the main segment 200. More specifically, a second portion 520 of the main segment 200 is angularly contorted (e.g., folded backward onto itself) so that the photodiodes 230 and 232 are positioned above the spectral light source(s) 162 and white light sources 260 and 262.

As further shown in FIG. 5, an outer portion 530 of the second circuit segment $210_2$ is contorted and angled in an inward direction (at transverse B) so that the second photodiode 232 of the second circuit segment $210_2$ faces outwardly in a desired direction toward a selected point of convergence and through the light pathway provided by the speculum 130 of FIG. 1. This point of convergence may correspond to an opening in the speculum attached to the interface 120 so as to enable light emitted from the light sources 160, 260 and 262 to pass through the opening in the speculum 130 and enable the photodiodes 230 and 232 to receive reflected return light. Similarly, an outer portion 540 of the first circuit segment $210_1$ is contorted and angled inwardly (at transverse C) so that the first photodiode 230 of the first circuit segment $210_2$ faces outwardly toward the point of convergence.

Additionally, for one embodiment of the disclosure, the amplifier 225 may be positioned in relation to the photodiodes 230 and 232 so that a portion of the second insulation layer 460 (or combination insulation/shielding layer) of the flexible circuit 170 at a contact area 550 for the amplifier 225 is interposed between the amplifier 225 and the first photodiode 230. Also, an end portion 174 of the main segment 200 beyond the contact area 550 of the amplifier 225 is folded back with the third insulation layer 470 toward the second end 174 of the main segment 200 being positioned in contact with and adjacent to the amplifier 225.

Lastly, as shown in FIG. 5, the pattern 500 may include the fourth circuit segment $210_4$ that is contorted and angled in an outward direction at transverse D, and thereafter, the fourth circuit segment $210_4$ is contorted to at least partially circumscribe the second portion 520 of the main segment 200 and the first circuit segment $210_1$, second circuit segment $210_2$ and third circuit segment $210_3$ extending therefrom, especially the photodiodes 230 and 232, the amplifier 225 and/or the spectral light source 162.

Referring now to FIG. 6, a perspective view of the flexible circuit 170 of FIG. 5 installed within the head portion 110 of the diagnostic tool 100 (e.g., otoscope head of the otoscope 100) is shown. The head portion 110 is an elongated, conical member 600 with one or more prefabricated shelf members 610 to support portions of the main segment 620 and 630 operating as an area of intersection between the main segment 200 and the first and second circuit segments $210_1$ and $210_2$, respectively. This pre-fabricated shelf members 610 are used to maintain photodiodes 230 and 232 to remain aimed toward a selected point of convergence operating as a light pathway provided by the speculum 130 of FIG. 1. Also, one of the prefabricated shelf members 610 (e.g., shelf member 615) provides a surface upon which the amplifier 225, longitudinally circumscribed by a portion of the main segment 200, is mounted.

Furthermore, the white light sources 260 and 262 of FIG. 3 may be aimed toward the point of convergence and the spectral light source 162 of FIG. 3 may be aimed toward the point of convergence as well. As shown, the light sources (e.g., white light sources 260, 262 of FIG. 5; spectral illumination light source 162) may be positioned in front of a planar surface 640 at the end of the conical member 600. Each of the photodiodes 230 and 232 and the spectral light source 162 are aligned with a corresponding pre-fabricated spacing 180 within the interface 120. Such spacings 180 are sized and located to receive with protruding portions of the spectral light source 162 and the photodiodes 230 and 232 for ease of assembly and assurances that the spectral illumination light source 162 and the photodiodes 230 and 232 are properly directed to emit incident light and receive reflected light from the body cavity (e.g., ear cavity) through the speculum 130 removably attached to an opposite end of the interface 120, as shown collectively in FIGS. 1 & 6.

As shown, the main segment 200 of the flexible circuit 170 may extend into the handle 150 with the first end 172 of the main segment 200 connected to the control circuitry 190, such as the power source 192, the controller 194, the network interface 196 and the storage memory 198. The controller 194 may be any type of data processing circuitry, which may include, but is not limited or restricted to a hardware processor (e.g., microprocessor with one or more processor cores, a digital signal processor, a programmable gate array, a microcontroller, an application specific integrated circuit "ASIC", etc.) with access to a data store (or a network connection to remote storage) to obtain the reference metric distributions for use in analysis of characteristics of the reflectance spectra determined from the reflected light collected by the photodiodes 230 and 232 to the reference metric distributions, inclusive of data associated with known reflectance spectra associated with healthy and/or unhealthy ear conditions. Also, the network interface 196 may provide wireless connectivity to a network or may provide a physical connector (e.g., Universal Serial Bus "USB connector, Apple® Lightning connector, etc.) for coupling to a computing device (e.g., computer, cellular telephone, wearable, server, video game console, etc.) for use in uploading data (e.g., data associated with characteristics of the reflectance spectra, and/or image(s) when video logic is deployed within the diagnostic tool 100) to a targeted computing device of a health service provider, insurance company, pharmacy or the like. As a result, the diagnostic tool 100 supports telemedicine.

In another embodiment, the preassembled interface 120 may be configured with some or all of the electronic components 160. Some of these OS components 160 may be retained the spacings 180 in the interface 120. At manufacture, the electronic component 160 installed within the interface 120 would be electrically coupled (e.g., using via and solder, or other electrical connection) to the flexible circuit 170.

Referring to FIG. 7, a second illustrative embodiment of a diagnostic tool 700 for for diagnosing health conditions, such as ear conditions irrespective of presence of cerumen in an ear canal, is shown. The diagnostic tool 700 may feature a component architecture that is identical to the diagnostic tool 100 of FIG. 1, except for the presence of visualization optics 140. As a result, the diagnostic tool 700 is specifically considered for OM detection without any visualization optics.

According to one embodiment, in lieu of visualization optics 140, the diagnostic tool 700 may be configured with a display 710 that is powered by the power source 192 via the flexible circuit 170 as well as coupled to video logic positioned within the housing 720, as described above. The display 710 may be a liquid crystal display (LCD), a type of light-emitting diode (LED) display such as OLED display, or the like. The display 710 provides the user, after depressing the measure button 155, with results of analyses produced by the controller 194 associated with the health of a portion of a tissue under inspection (e.g., portion of the middle ear). The results may include, but are not limited or restricted to (i) a presence or absence of OM, (ii) a measured temperature as provided from the temperature sensor, (iii) an image of the tissue under inspection as captured by the video logic or the like.

In the foregoing description, the invention is described with reference to specific exemplary embodiments thereof. However, it will be evident that various modifications and changes may be made thereto without departing from the broader spirit and scope of the invention as set forth in the appended claims.

What is claimed is:

1. A diagnostic tool, comprising:
a handle including a controller;
a head portion coupled to the handle, the head portion comprises one or more optical spectroscopy (OS) components including at least one light detection element and an amplifier, wherein signals generated by the at least one light detection element are amplified by the amplifier; and
a circuit including a plurality of layers in physical contact, the plurality of layers comprises at least one shielding layer interposed between signal lines and sources of external electromagnetic interference, the circuit further including a first contact area upon which the at least one light detection element is placed and a second contact area upon which the amplifier is placed,
wherein one or more portions of the circuit positioned within the head portion are configured to be contorted at acute through reflex angles while maintaining electrical connectivity between the controller, the one or more OS components and the amplifier.

2. The diagnostic tool of claim 1, wherein the at least one light detection element includes at least one photodiode.

3. The diagnostic tool of claim 2, wherein the circuit being contorted and placed in a folded state, wherein a distance between the at least one photodiode and the amplifier when the circuit is placed in the folded state is less than a distance between the at least one photodiode and the amplifier when the circuit is placed in the unfolded state.

4. The diagnostic tool of claim 1, wherein the one or more OS components further include a spectral illumination source to emit incident light and the at least one light detection element to collect the incident light upon reflection and the circuit including a second contact area for the spectral illumination source.

5. The diagnostic tool of claim 4, wherein the spectral illumination source and the at least one light detection element are directed to a point of convergence.

6. The diagnostic tool of claim 5, wherein the point of convergence corresponds to an opening through a light pathway provided by a speculum, the speculum being coupled to the head portion.

7. The diagnostic tool of claim 1 further comprising a waveguide coupled to the at least one light detection element.

8. The diagnostic tool of claim 1, wherein the circuit is contorted to partially surround the amplifier with a first portion of the second contact area of the circuit being attached to a first side of the amplifier and a different area of the circuit being positioned against a second side of the amplifier opposite the first side of the amplifier.

9. An otoscope comprising:
a handle including a controller;
a head portion coupled to the handle, the head portion comprises one or more optical spectroscopy (OS) components including a spectral light source to emit incident light to inspect a portion of an ear, at least one light detection element to detect reflected light resulting from the incident light emitted into the portion of the ear, and an amplifier to increase amplitude of signals generated by the at least one light detection element; and
a circuit including a plurality of layers in physical contact that include at least one shielding layer interposed between signal lines and sources of external electromagnetic interference, the circuit including a first contact area upon which the at least one light detection element is placed and a second contact area upon which the amplifier is placed,
wherein one or more portions of the circuit positioned within the head portion are contorted at acute through reflex angles that alter the circuit from an unfolded state to a folded state while maintaining electrical connectivity between the controller and the one or more OS components and the amplifier.

10. The otoscope of claim 9, wherein the at least one light detection element includes at least one photodiode configured to detect the reflected light in a wavelength range between at least four-hundred nanometers and two-thousand (2000) nanometers.

11. The otoscope of claim 10 further comprising:
a speculum coupled to the head portion.

12. The otoscope of claim 11, wherein the spectral illumination source and the at least one photodiode are directed to a point of convergence corresponding to an opening through a light pathway provided by the speculum.

13. The otoscope of claim 12, wherein the waveguide corresponds to one or more plastic or glass optical fibers and the plurality of layers correspond to the circuit.

14. The otoscope of claim 13, wherein the spectral light source is attached to a third contact area of the circuit.

15. The otoscope of claim 14, wherein the controller is configured to receive data associated with the reflected light captured by the at least one photodiode and conduct an analysis of the data associated with the reflected light, the analysis includes assessing characteristics gathered from the reflected light, including data associated with a shape or magnitude of a reflectance spectra associated with the reflected light, for correlation with data associated with prior measured reflectance spectra for ears with health conditions including Otitis Media.

16. The otoscope of claim 14, wherein the controller to further conduct the analysis of the data associated with the reflected light by conducting an analysis to determine a correlation between the characteristics gathered from the reflected light metrics to data associated with prior measured reflectance spectra for ears with no health conditions.

17. The circuit of claim 16, wherein the main circuit segment includes a first portion including the first contact area and a second portion including a connector adapted for electrical coupling to circuitry that controls operability of (i) the spectral illumination source, or (ii) the at least one light detection element, or (iii) both the spectral illumination source and the at least one light detection element.

18. A circuit comprising:
a main circuit segment extending in a longitudinal direction, the main circuit segment including a first contact area to which an amplifier is coupled;
a plurality of circuit segments extending laterally from the main circuit segment, the plurality of circuit segments including a second contact area to which a spectral illumination source is coupled and a third contact area to which at least one light detection element is attached,
wherein each of the main circuit segment and the plurality of circuit segments includes a plurality of layers that are in physical contact and include at least a trace layer and shielding layer covering at least a top surface and a bottom surface of the trace layer so that the shielding layer is interposed between the trace layer and sources of external electromagnetic interference, each of the main circuit segment and the plurality of circuit segments is contorted into a folded state for placement within a head portion of a diagnostic tool so that both the spectral illumination source and the at least one light detection element are directed to a point of convergence.

19. The circuit of claim 18, wherein the first contact area being configured to receive and retain the amplifier positioned a first prescribed distance from the at least one light detection element.

20. The circuit of claim 19, wherein the amplifier is positioned a second prescribed distance from the at least one light detection element when the circuit is placed into the folded state, the second prescribed distance being less than the first prescribed distance.

* * * * *